(12) United States Patent
Liu et al.

(10) Patent No.: US 8,734,816 B2
(45) Date of Patent: May 27, 2014

(54) POROUS NANOPARTICLE SUPPORTED LIPID BILAYER NANOSTRUCTURES

(75) Inventors: Juewen Liu, Kitchener (CA); Jeffrey C. Brinker, Albuquerque, NM (US); Carlee Ashley, Albuquerque, NM (US); Eric C. Carnes, Albuquerque, NM (US)

(73) Assignees: STC.UNM, Albuquerque, NM (US); Sandia Corporation, Albuquerque, NM (US)

( * ) Notice: Subject to any disclaimer, the term of this patent is extended or adjusted under 35 U.S.C. 154(b) by 0 days.

(21) Appl. No.: 13/143,164

(22) PCT Filed: Jan. 5, 2010

(86) PCT No.: PCT/US2010/020096
§ 371 (c)(1),
(2), (4) Date: Jul. 1, 2011

(87) PCT Pub. No.: WO2010/078569
PCT Pub. Date: Jul. 8, 2010

(65) Prior Publication Data
US 2011/0268791 A1    Nov. 3, 2011

Related U.S. Application Data

(60) Provisional application No. 61/142,495, filed on Jan. 5, 2009.

(51) Int. Cl.
*A61K 9/127* (2006.01)
*A61K 9/51* (2006.01)

(52) U.S. Cl.
USPC ........... 424/400; 424/417; 424/422; 424/484; 424/489; 424/490

(58) Field of Classification Search
USPC .................. 424/400, 417, 422, 484, 489, 490
See application file for complete search history.

(56) References Cited

U.S. PATENT DOCUMENTS

| 2006/0154069 A1* | 7/2006 | Lin et al. ................ 428/402 |
| 2008/0095852 A1 | 4/2008 | Kong et al. |
| 2008/0213377 A1* | 9/2008 | Bhatia et al. ................ 424/489 |

FOREIGN PATENT DOCUMENTS

| WO | WO 00/76556 | * 12/2000 | ............ A61K 51/04 |
| WO | 03055469 | 7/2003 | |

OTHER PUBLICATIONS

Buranda et al, Langmuir 19:1654-1663, 2003.*
Slowing, Igor I. at al., "Mesoporous silica nanoparticles as controlled release drug delivery and gene transfection carriers", Advanced Drug Delivery Reviews, 60, 2008, 1278-1288.
Fishkis, Maya, "Steps Towards the Formation of a Protocell; The Possible Role of Short Peptides", Orig Live Evol Biosph, 2007, 37537-553.

* cited by examiner

*Primary Examiner* — Kevin Hill
(74) *Attorney, Agent, or Firm* — Henry D. Coleman; R. Neil Sudol

(57) ABSTRACT

Various exemplary embodiments provide protocell nanostructures and methods for constructing and using the protocell nanostructures. In one embodiment, the protocell nanostructures can include a core-shell structure including a porous particle core surrounded by a shell of lipid bilayer(s). The protocell can be internalized in a bioactive cell. Various cargo components, for example, drugs, can be loaded in and released from the porous particle core of the protocell(s) and then delivered within the bioactive cell.

14 Claims, 4 Drawing Sheets

US 8,734,816 B2

POROUS NANOPARTICLE SUPPORTED LIPID BILAYER NANOSTRUCTURES

RELATED APPLICATIONS

This application claims priority from U.S. Provisional Patent Application Ser. No. 61/142,495, filed Jan. 5, 2009, which is hereby incorporated by reference in its entirety.

GOVERNMENT RIGHTS

This invention was made with Government support under Contract No. PHS 2 PN2 EY016570B awarded by the National Institutes of Health (NIH). The U.S. Government has certain rights in the invention.

FIELD OF THE INVENTION

This invention relates generally to nanostructures and, more particularly, to protocells having a porous particle supported lipid bilayer, and methods for forming and using the protocells.

BACKGROUND OF THE INVENTION

One of the challenges in nanomedicine is to engineer nanostructures and materials that can efficiently encapsulate cargo, for example, drugs, at high concentration, cross the cell membrane, and controllably release the drugs at the target site over a prescribed period of time. Recently, inorganic nanoparticles have emerged as a new generation of drug or therapy delivery vehicles in nanomedicine. More recently, gating methods that employ coumarin, azobenzene, rotaxane, polymers, or nanoparticles have been developed to seal a cargo within a particle and allow a triggered release according to an optical or electrochemical stimulus.

While liposomes have been widely used in drug delivery due to their low immunogenicity and low toxicity, they still need to be improved in several aspects. First, the loading of cargo can only be achieved under the condition in which liposomes are prepared. Therefore, the concentration and category of cargo may be limited. Second, the stability of liposomes is relatively low. The lipid bilayer of the liposomes often tends to age and fuse, which changes their size and size distribution. Third, the release of cargo in liposomes is instantaneous upon rupture of the liposome which makes it difficult to control the release.

Thus, there is a need to overcome these and other problems of the prior art and to provide a nanostructure including a porous core and methods for forming and using the nanostructure.

SUMMARY OF THE INVENTION

According to various embodiments, the present teachings include a protocell nanostructure. The protocell nanostructure can include a porous particle core and at least one lipid bilayer surrounding the porous particle core to form a protocell. The protocell can be capable of loading one or more cargo components to the pores of the porous particle core and releasing the one or more cargo components from the porous particle core across the surrounding lipid bilayer.

According to various embodiments, the present teachings also include a method of forming a loaded protocell. The method can begin with providing a porous particle core, a lipid bilayer, and a cargo component. The lipid bilayer can then be fused to surround the porous particle core and the cargo component can be synergistically loaded into one or more pores of the porous particle core. A loaded protocell can thus be formed.

According to various embodiments, the present teachings further include a method for delivering a cargo component using a protocell. In this method, a porous particle core, a lipid bilayer, and one or more cargo components can be provided to fuse the lipid bilayer onto the porous particle core and to synergistically load the one or more cargo components into one or more pores of the porous particle core to form a loaded protocell. A bioactive cell can then be incubated with the loaded protocell to internalize the loaded photocell within the bioactive cell. Following the internalization, the lipid bilayer of the loaded photocell can be ruptured by applying a surfactant in preparation for transporting the one or more cargo components from the porous particle core into the bioactive cell. Various embodiments can thus include a delivery system according to the method of using protocells.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

DESCRIPTION OF THE EMBODIMENTS

Reference will now be made in detail to the exemplary embodiments of the invention, examples of which are illustrated in the accompanying drawings. Wherever possible, the same reference numbers will be used throughout the drawings to refer to the same or like parts. In the following description, reference is made to the accompanying drawings that form a part thereof, and in which is shown by way of illustration specific exemplary embodiments in which the invention may be practiced. These embodiments are described in sufficient detail to enable those skilled in the art to practice the invention and it is to be understood that other embodiments may be utilized and that changes may be made without departing from the scope of the invention. The following description is, therefore, merely exemplary.

Various embodiments provide nanostructures and methods for constructing and using the nanostructures. In one embodiment, the nanostructures can include, for example, a core-shell structure including a porous particle core surrounded by a shell of lipid bilayer(s). The porous particle core can include, for example, a porous nanoparticle made of an inorganic or organic material. In various embodiments, such nanostructures can also be referred to as "protocells" or "functional protocells," since the "protocells" can mimic bioactive cells (or real cells) to have a supported lipid bilayer membrane structure.

In embodiments, the porous particle core of the protocells can be loaded with various desired species, which are also referred to herein as "cargo" or "cargo components". In embodiments, the cargo components can include, but are not limited to, chemical molecules, nucleic acids, therapeutic agents, and/or other nanoparticles, which are useful for a wide range of applications, such as, for example, biomedical diagnostics, imaging, disease treatment, drug delivery, and anti-bacteria applications.

In embodiments, the lipid bilayer of the protocells can provide biocompatibility and can be modified to possess targeting species including, for example, targeting peptides, antibodies, aptamers, and PEG (polyethylene glycol) to allow, for example, further stability of the protocells and/or a targeted delivery into a bioactive cell.

Figure 1:
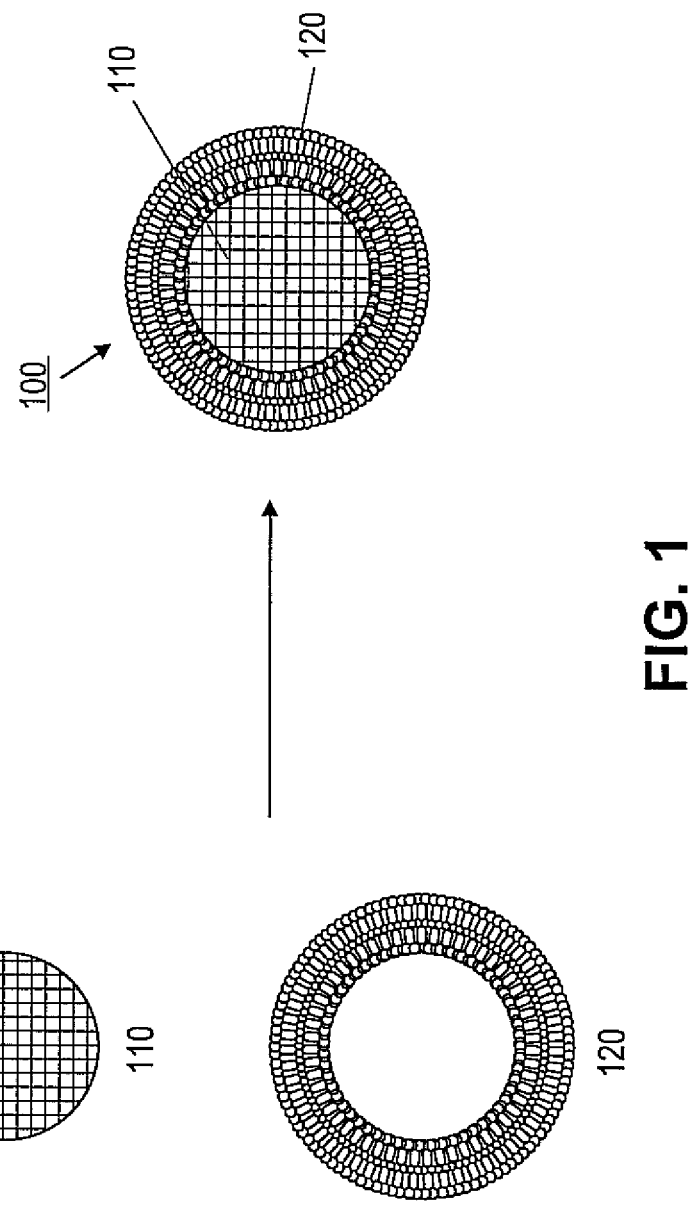
FIG. 1 depicts a schematic of an exemplary protocell nanostructure as well as its formation in accordance with the present teachings.

FIG. 1 depicts a schematic of an exemplary protocell and its formation in accordance with the present teachings. As shown, the exemplary protocell 100 can include, for example, at least one lipid bilayer 120 surrounding a porous particle core 110 to form a supported lipid bilayer on the porous particle core.

In embodiments, the porous particle core 110 can include porous nanoparticles having at least one dimension, for example, a width or a diameter of about 3000 nm or less, or about 1000 nm or less, or about 100 nm or less. For example, the porous particle core 110 can have a particle diameter ranging from about 30 nm to about 3000 nm. In embodiments, the porous particle core 110 can have various cross-sectional shapes including a circular, rectangular, square, or any other shape.

In embodiments, the porous particle core 110 can have pores with a mean pore size ranging from about 2 nm to about 30 nm, although the mean pore size and other properties (e.g., porosity of the porous particle core) are not limited in accordance with various embodiments of the present teachings.

In embodiments, the porous particle core 110 can be made of various materials, inorganic or organic, such as, for example, silica, alumina, titania, zirconia, polymers (e.g., polystyrene), or combinations thereof. In embodiments, the porous particle core 110 can include inorganic particles, polymer hydrogel particles or other suitable particles.

In embodiments, the porous particle core 110 can be biocompatible. Drugs and other cargo components can be loaded by adsorption and/or capillary filling of the pores of the particle core. In embodiments, the loaded cargo can be released from the porous surface of the particle core 110, wherein the release profile can be determined or adjusted by, for example, the pore size, the surface chemistry of the porous particle core, the pH value of the system, and/or the interaction of the porous particle core with the surrounding lipid bilayer(s).

In various exemplary embodiments, the porous particle core 110 can include, for example, mesoporous silica particles that can provide biocompatibility and precisely defined nanoporosity. In embodiments, the mesoporous silica particles can be prepared, for example, by mixing HCl, ethanol, cetyltrimethylamonium bromide (CTAB), and/or tetraethyl orthosilicate (TEOS). In embodiments, the mesoporous silica particles can be prepared by surfactant templated aerosol-assisted self-assembly method as described in a journal paper from Nature 1999, vol. 398, page 223-226, entitled "Aerosol-Assisted Self-Assembly of Mesostructure Spherical Nanoparticles," which is hereby incorporated by reference in its entirety. In this example, after removal of surfactant templates, hydrophilic nanoparticles characterized by a uniform, ordered, and connected mesoporosity can be prepared with a specific surface area of, for example, about 935 m$^2$/g.

In embodiments, the porous particle core 110 can be hydrophilic and can be further treated to provide a more hydrophilic surface. For example, mesoporous silica particles can be further treated with ammonium hydroxide and hydrogen peroxide to provide a high hydrophilicity.

Referring back to FIG. 1, the lipid bilayer 120 can be fused onto the porous particle core 110 to form the protocell 100. In embodiments, the lipid bilayer 120 can include a phospholipid including, but not limited to, 1,2-Dioleoyl-3-Trimethylammonium-Propane (DOTAP), 1,2-Dioleoyl-sn-Glycero-3-Phosphocholine (DOPC) or a combination thereof.

In embodiments, the lipid bilayer 120 can be prepared, for example, by extrusion of hydrated lipid films through a filter with pore size of, for example, about 100 nm, using standard protocols. The filtered lipid bilayer films can then be fused with the porous particle cores, for example, by a pipette mixing.

In embodiments, excess amount of lipid bilayers 120 or the exemplary lipid bilayer films can be used to form the protocell 100 in order to improve the protocell colloidal stability.

In embodiments, various dyes or fluorescences can be attached to the porous particle core 110 and/or the lipid bilayer 120 for analyzing the formed protocell nanostructure. For example, the porous particle core can be a silica core and can be covalently labeled with FITC (green fluorescence), while the lipid bilayer can be labeled with Texas red (red fluorescence). The porous particle core, the lipid bilayer and the formed protocell can then be observed by, for example, confocal fluorescence microscopy.

Figure 2:
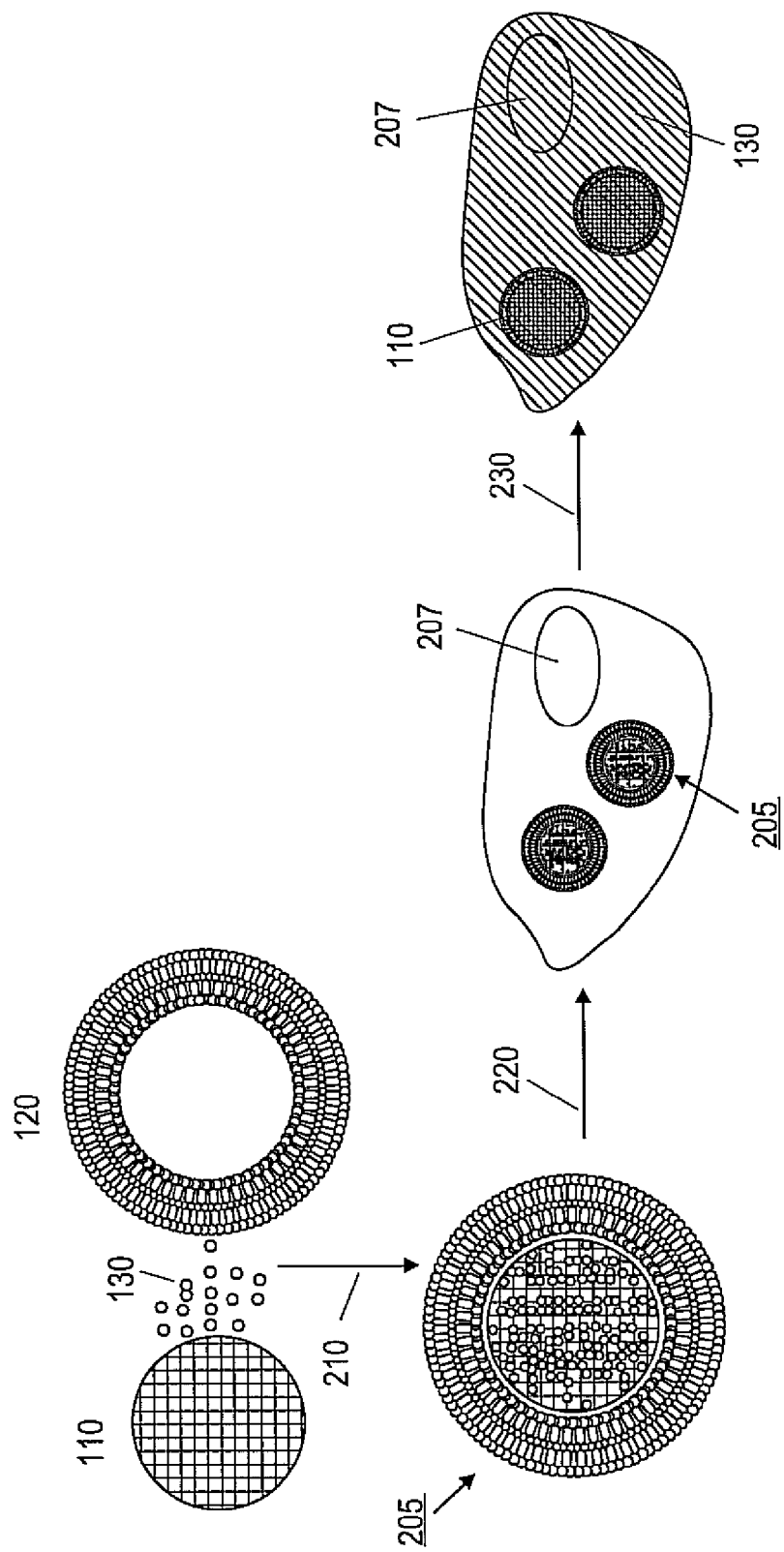
FIG. 2 depicts an exemplary protocell delivery system in accordance with the present teachings.

In various embodiments, the protocell 100 can be a synergistic system where the lipid bilayer fusion or liposome fusion (i.e., on the porous particle core) can load and seal various cargo components 130 into the pores of the particle core 110, creating a loaded protocell useful for cargo delivery across the cell membrane of the lipid bilayer. For example, FIG. 2 depicts an exemplary delivery system and its method in accordance with various embodiments of the present teachings. In embodiments, in addition to fusing a single lipid (e.g., phospholipids) bilayer, multiple bilayers with opposite charges can be successively fused onto the porous particle core to further influence cargo loading and/or sealing.

At 210 of FIG. 2, a fusion and synergistic loading mechanism can be included for the exemplary cargo delivery. For example, cargo 130, can be loaded, encapsulated, or sealed, synergistically through liposome fusion on the exemplary porous particles 110. The cargo 130 can include, for example, peptides, proteins, antibodies, DNAs, RNAs, fluorescent dyes, inorganic nanoparticles that include gold nanoparticles, magnetic nanoparticles or quantum dots, and/or drugs such as chemotherapeutic drugs, hydrophobic anti-cancer drugs or other types of drugs.

In embodiments, the cargo 130 can be loaded into the pore of porous particle cores 110 to form the loaded protocell 205, which is different from bioactive cells that have an aqueous interior area but do not include particle nanopores. In various embodiments, any conventional technology that is developed for liposome-based drug delivery, for example, targeted delivery using PEGylation, can be transferred and applied to the disclosed porous particle supported lipid bilayers, i.e., the protocells. In an exemplary embodiment, versatile loading with improved bilayer stability can be achieved for the protocell 100.

In various embodiments, electrostatics and pore size can play a role in cargo loading. For example, porous silica nanoparticles can carry a negative charge and the pore size can be tunable from about 2 nm to about 10 nm. Such negatively charged nanoparticles can have a natural tendency to adsorb positively charged molecules. In an exemplary embodiment, a chemotherapeutic drug doxocubicin (red fluorescence) that carries a positive charge can be adsorbed by porous silica. After fusion with an NBD (green fluorescence)-labeled DOPC liposome, the red-in-green core-shell structure can be observed under fluorescence microscopy. In various embodiments, other properties such as surface wettability (e.g., hydrophobicity) can also affect loading cargo with different hydrophobicity.

In various embodiments, the cargo loading can be a synergistic lipid-assisted loading by tuning the lipid composition. For example, if the cargo component is a negatively charged molecule, the cargo loading into a negatively charged silica can be achieved by the lipid-assisted loading. In an exemplary embodiment that is absent of lipid, the silica particle can not adsorb any exemplary calcein molecule, which is also negatively charged. However, in the presence of DOTAP lipid (e.g., labeled with Texas red, the red fluorescence dye), the negatively charged calcein dye (green fluorescence) can be loaded into the pores of the negatively charged silica particle when the lipid bilayer is fused onto the silica surface showing a fusion and synergistic loading mechanism.

In this manner, fusion of a non-negatively charged (i.e., positively charged or neutral) lipid bilayer or liposome on a negatively charged mesoporous particle can serve to load the particle core with a negatively charged dye or other negatively charged cargo components. The negatively charged cargo components can be concentrated in the loaded protocell having a concentration exceed about 100 times as compared with the charged cargo components in a solution.

At 220, the loaded protocells 205 can have a cellular uptake for cargo delivery into desirable site. For example, the cargo-loaded protocells 205 can be incubated with a desirable bioactive cell 207 and can be internalized or uptaken by the bioactive cell 207, for example, a mammalian cell.

Due to the internalization of cargo-loaded protocells 205 in the bioactive cell 207, cargo components 130 can then be delivered into the bioactive cell 207. For example, when free calcein cargo is mixed with Chinese Hamster Ovary (CHO) cells, the CHO cells can not take the green dye calcein because calcein is a membrane impermeable dye. However, calcein can be taken into the CHO cells through the internalized protocells that is loaded with green dye calcein. The CHO cells can then be observed green (not shown) due to the delivery of the green dye calcein.

In another example, negatively charged DNA itself can not be directly delivered or internalized into the bioactive cells. However, the negatively charged DNA can be loaded first into a protocell and then into bioactive cells through the internalization of the loaded protocells. As such, loaded protocells can deliver the exemplary calcein or negatively charged DNA into bioactive cells, e.g., CHO.

In various embodiments, the protocells and/or the loaded protocells can provide a targeted delivery methodology for selectively delivering the protocells or the cargo components to targeted bioactive cells (e.g., cancer cells). For example, a surface of the lipid bilayer can be modified by a targeting active species that corresponds to the targeted bioactive cell 207.

Figure 3:
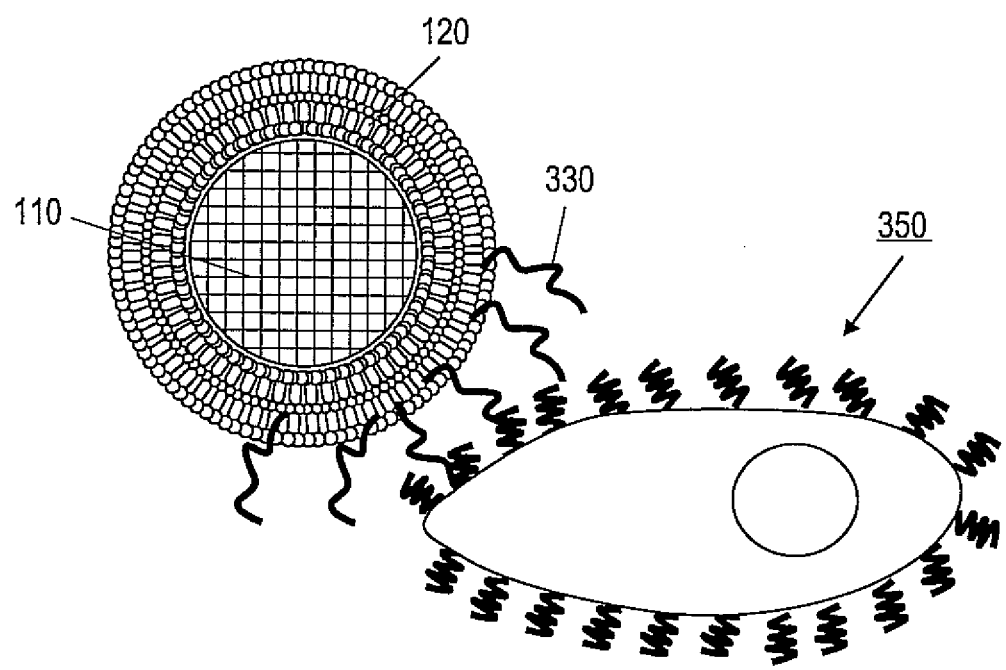
FIG. 3 is a schematic showing surface re-organization of targeting ligands on a protocell to bind a targeted bioactive cell in accordance with the present teachings.

For example, FIG. 3 depicts a schematic showing re-organization of an exemplary targeting active species to bind a targeted bioactive cell 350 in accordance with the present teachings. In one embodiment, by conjugating an exemplary targeting peptide SP94 (see 330 of FIG. 3) that targets cancer liver cells to the lipid bilayer 120 of the protocells 100 or the loaded protocells 205 (see FIG. 2), a large number of protocells can be recognized and internalized by this specific cancer cells (see 350 of FIG. 3) due to the specific targeting of the exemplary SP94 peptide with the liver cancer cells. In some cases, if the protocells are not conjugated with the targeting peptide, if the peptide is a non-targeting peptide to the targeted liver cancer cell, or if the liver cancer cells are normal liver cells, there can be no significant association, uptake or internalization of the protocells or the loaded protocells by the cancer cells.

In various embodiments, the protocells and/or the loaded protocells can provide a ligand display and/or a multivalent targeting on a fluidic interface of the lipid bilayer. For example, displaying multiple copies of the targeting peptide on the protocell surface can allow multivalent targeting. Different from other displaying platforms, protocells can have a unique fluidic phospholipid bilayer surface, which allows re-organization of ligands in response to targets. Such re-organization can allow high affinity multivalent binding at low overall ligand density, which may decrease the immune response of host cells.

Referring back to FIG. 2, at 230, the cellular uptaken protocells 205 can release cargo components 130 from the porous particle 110 and transport the released cargo components into the bioactive cell 207. For example, sealed within the protocell by the liposome fusion on the porous particle core, the cargo components 130 can be released from the porese, transported across the protocell membrane of the lipid bilayer 120 and delivered within the bioactive cell 207.

Figure 4A:
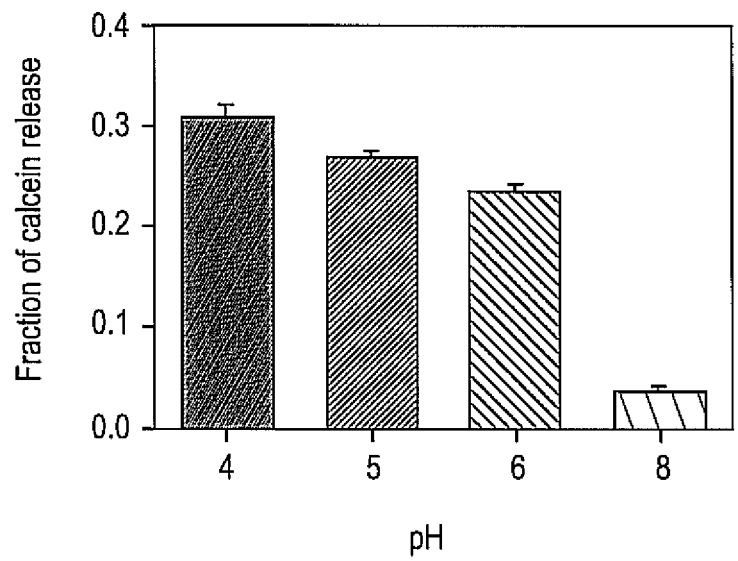
FIGS. 4A-4B depict release profiles of exemplary calcein loaded protocells in accordance with the present teachings.
Figure 4B:
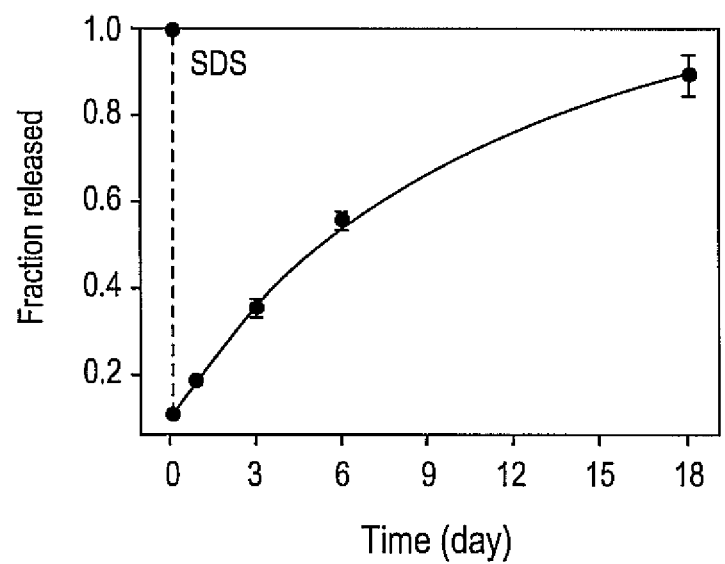

In embodiments, the release profile of cargo components in protocells can be more controllable as compared with when only using liposomes as known in the prior art. The cargo release can be determined by, for example, interactions between the porous core and the lipid bilayer and/or other parameters such as pH value of the system. For example, the release of doxocubicin cargo can be achieved through dissolution of porous silica; while the release of calcein cargo in the synergistically loaded protocells can be pH-dependent as shown in FIGS. 4A-4B.

In embodiments, the pH value for releasing calcein cargo can be of about pH 14 or less. As shown in FIG. 4A, lower pHs can facilitate the release of calcein cargo more as compared with high pHs. This is advantageous because the endosomal compartments inside cells can be at low pHs. FIG. 4B shows a calcein cargo release at a specific pH value of about 7.4, wherein the release can span for about 20 days.

In embodiments, surfactants can be applied to rupture the lipid bilayer or the liposome, transporting the cargo components across the liposome within the bioactive cell. In exemplary embodiments, the phospholipid bilayer of the protocells can be ruptured by applying a surfactant of sodium dodecyl sulfate (SDS). In embodiments, the rupture of the lipid bilayer can in turn induce immediate and complete release of the cargo components from the pores of the particle core of the protocells.

In this manner, the protocell platform can provide versatile delivery systems as compared with other delivery systems in the art. For example, when compared to delivery systems using nanoparticles only, the disclosed protocell platform can provide a simple system and can take advantage of the low toxicity and immunogenicity of liposomes or lipid bilayers along with their ability to be PEGylated or to be conjugated to extend circulation time and effect targeting. In another example, when compared to delivery systems using liposome only, the protocell platform can provide a more stable system and can take advantage of the mesoporous core to control the loading and/or release profile.

In addition, the lipid bilayer and its fusion on porous particle core can be fine-tuned to control the loading, release, and targeting profiles. Further, the lipid bilayer can provide a fluidic interface for ligand display and multivalent targeting, which allows specific targeting with relatively low surface ligand density due to the capability of ligand re-organization on the fluidic lipid interface. Furthermore, the disclosed protocells can readily enter bioactive cells while empty liposome without the support of porous particles cannot be internalized by the cells.

The following examples are illustrative of the invention and its advantageous properties, and are not to be taken as limiting the disclosure or claims in any way. In the examples, as well as elsewhere in this application, all parts and percentages are by weight unless otherwise indicated.

EXAMPLES

Example 1

Materials

Exemplary phospholipids were obtained from Avanti Polar Lipids Inc. (Alabaster, Ala.). Exemplary cholesterol was obtained from Sigma (St. Louis, Mo.). Texas Red-labeled DHPE lipid and fluorescein isothiocyanate (FITC) were obtained from Invitrogen (Carlsbad, Calif.). All silanes and calcein were obtained from Aldrich Sigma (St. Louis, Mo.). Chinese Hamster Ovary (CHO) cells and cell culture related chemicals and media were obtained from American Type Culture Collection (ATCC).

All UV-vis absorption data were collected on a Perkin-Elmer spectrophotometer; all fluorescence data were obtained on a Horiba Jobin Yvon Fluoromax-4 fluorometer; and all light scattering data were collected on a Zetasizer Nano dynamic light scattering instrument (Malvern).

Lipids and other chemicals used in the examples included the following:

DOTAP:
1,2-Dioleoyl-3-Trimethylammonium-Propane
(Chloride Salt)

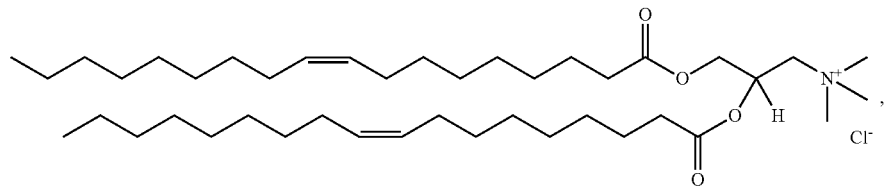 [SMILES: CCCCCCCC/C=C\CCCCCCCC(=O)OCC(C[N+](C)(C)C)OC(=O)CCCCCCC/C=C\CCCCCCCC ; [Cl-]]

DOPC: 1,2-Dioleoyl-sn-Glycero-3-Phosphocholine

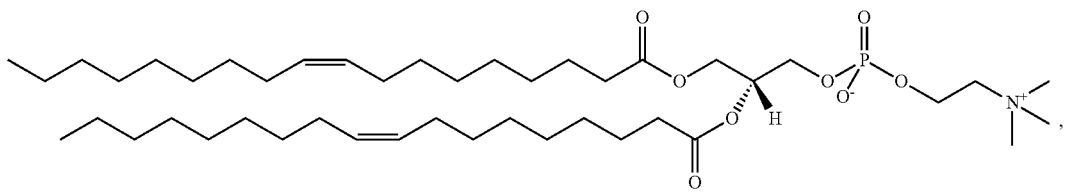 [SMILES: CCCCCCCC/C=C\CCCCCCCC(=O)OC[C@H](COP(=O)([O-])OCC[N+](C)(C)C)OC(=O)CCCCCCC/C=C\CCCCCCCC]

DOPS:
1,2-Dioleoyl-sn-Glycero-3-[Phospho-L-Serine]
(Sodium Salt)

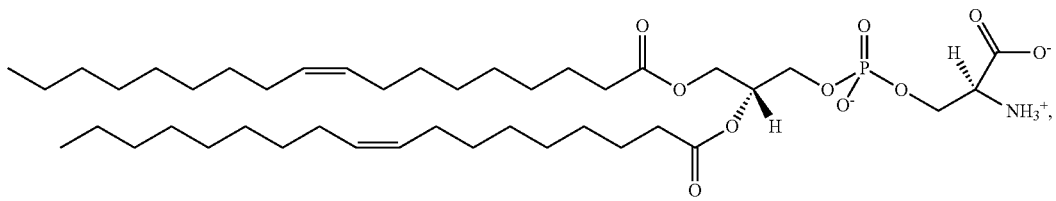

Texas Red@DHPE: Texas Red@

1,2-dihexadecanoyl-sn-glycero-3-phosphoethanolamine, triethylammonium salt

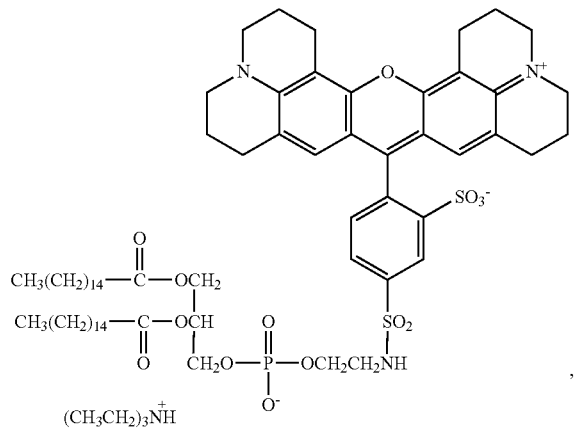

and
Cholesterol

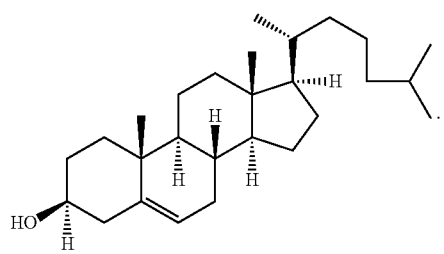

Example 2

Preparation of Mesoporous Silica Nanoparticles

Mesoporous silica nanoparticles were prepared by the aerosol-assisted self-assembly method, wherein silica/surfactant aerosols were generated using a commercial atomizer (Model 9302A, TSI, Inc., St Paul, Minn.) operated with nitrogen as a carrier/atomization gas. The reaction was started with a homogeneous solution of soluble silica precursor tetraethyl orthosilicate (TEOS), HCl, and surfactant prepared in an ethanol/water solution with an initial surfactant concentration much less than the critical micelle concentration. The pressure drop at the pinhole was about 20 psi. The temperature for the heating zones was kept at about 400° C. Particles were collected on a durapore membrane filter maintained at about 80° C. cetyltrimethylamonium bromide (CTAB) was selected as the structure directing template.

In a typical synthesis of mesoporous silica nanoparticles, about 55.9 mL $H_2O$, about 43 mL ethanol, about 1.10 mL 1N HCl, about 4.0 g CTAB, and about 10.32 g TEOS were mixed. The mixture was also referred to as water/ethanol/HCl/CTAB/TEOS mixture.

To prepare FITC-labeled particles, 18 mg FITC and 100 μL 3-aminopropyltriethoxysilane (APTES) were reacted in about 1 mL 200 proof ethanol for about four hours in dark. The resultant solution along with about 36 μL of 12N HCl were then added to the water/ethanol/HCl/CTAB/TEOS mixture to make FITC-labeled particles.

The reaction between FITC and APTES is presented below.

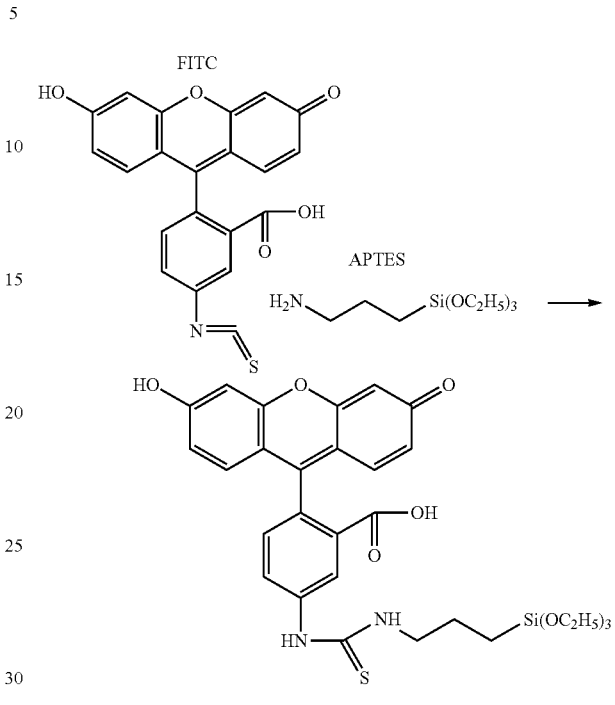

Example 3

Preparation of Liposomes

Phospholipids were dissolved in chloroform at concentrations of about 10 to about 25 mg/mL. Aliquots were dispensed into scintillation vials so that each vial contained 2.5 mg lipids. For mixed lipids, the total amount of lipids was also controlled to be about 2.5 mg per vial. Some lipids were mixed with a small fraction (2-5%) of Texas Red-labeled DHPE. The chloroform in the vials was evaporated under a nitrogen flow in a fume hood and lipid films were formed. The vials were then stored in a vacuum oven at room temperature overnight to remove any residual chloroform. The samples were frozen at about −20° C. before use.

To prepare lipid bilayers or liposomes, the vials were brought to room temperature and rehydrated by adding 1 mL of 0.5×PBS with occasional shaking for at least 1 hr, forming a cloudy lipid suspension. The suspension was extruded with a mini-extruder purchased from Ananti Polar Lipids. A membrane with pore diameter of 100 nm was used and at least ten extrusion cycles were performed. The resulting clear lipid bilayers or liposomes were stored in a new vial at 4° C. Light scattering experiments showed that the as-prepared liposomes have a mean hydrodynamic diameter of about 140 nm and the size distribution did not change after storing at about 4° C. for a week.

Example 4

Preparation of Supported Bilayers, the Protocells

The silica nanoparticles were weighed (about 25 to about 50 mg) and transferred into a scintillation vial. About 20 mL of 200 proof ethanol with 1% HCl was added and the solution was sonicated for at least 30 min to extract the CTAB surfactant from the pores. The particles were collected by centrifugation and removal of the supernatants. The washing process was repeated twice with ethanol and twice with water. To make the surface more hydrophilic, the particles were then treated with 4% ammonium hydroxide and 4% hydrogen peroxide at about 80° C. for about 10 min. After washing with water, the particles were further treated with 0.4 M HCl and 4% hydrogen peroxide at about 80° C. for about 10 min and washed with water. The final concentration of silica nanoparticles were made to be about 25 mg/mL in water.

Equal volumes (e.g., about 50 μL) of the above prepared silica nanoparticles and liposomes (e.g., about 2.5 mg/mL) were mixed by pipetting the mixture several times. The mixture was allowed to sit at room temperature for about 20 min with occasional agitation. Extra lipids were removed by centrifugation of the mixture at 4000 rpm for about 1 minute, and removal of the supernatant. The supported bilayers were subsequently washed with 200 μL it of 0.25×PBS and finally dispersed in 200 μL 0.25×PBS.

To prepare supported bilayers that encapsulate calcein, the silica nanoparticles were first mixed with 250 μM calcein and liposomes were subsequently added. The remaining procedures were the same as described above. Because DOTAP lipids showed the highest calcein encapsulation efficiency, most examples herein included the supported bilayers with DOTAP lipids.

Example 5

Cellular Uptake of Supported Bilayers (Protocells)

Cell Culture: Chinese Hamster Ovary cells (CHO) were obtained from the American Type Culture Collection (ATCC) and maintained in K-12 media supplemented with about 10% fetal bovine serum, about 1% penicillin and about 1% streptomycin. The media were changed every two to three days and the cells were passaged by trypsinization. To prepare samples for confocal imaging, round glass cover slips were used for cell growth. The glass slides were treated with 0.1M KOH for at least 24 hours before use. Cells in the media were dropped onto the cover slips and the slips were kept in Petri dishes. The cells were kept in an incubator at 37° C. with 5% $CO_2$ and 95% humidity.

Cellular uptake of supported bilayers (protocells): about 1 mL of serum free media was warmed to about 37° C. and about 10 μL of the above prepared supported bilayers were added and vortexed. To study the uptake of supported bilayers by CHO cells, the cells were grown to ~70% confluence. The old media was removed and fresh media with supported bilayers were introduced. The cells were incubated for about four hours at about 37° C. and free particles were washed away with PBS and media before imaging.

Example 6

Effect of Supported Bilayers on CHO Cell Viability

CHO cells were incubated with supported bilayers as described above. The media was removed and 300 μL viability dyes (0.5 μL calcein-AM and 2 μL ethidium homodimer dissolved in about 2 mL serum free media) were added. The cells were incubated at 37° C. for about 30 min. Fluorescence was monitored under an inverted fluorescence microscope. Viability assays indicated that more than 97% of the cells were viable.

Confocal fluorescence microscopy: A Bio-Rad Radiance 2100 confocal fluorescence microscope system was used for imaging cells. Argon 488 nm line was used for imaging FITC and calcein; green HeNe (543 nm) was used for imaging Texas Red; and Red Diode (633 nm) was used for DIC imaging. All images were collected with a 60× oil immersion objective. To image supported lipid bilayers, 3 μL of dilute protocells were spotted on a glass slide and sealed with a cover slip by super glue.

Example 7

Quantification of Calcein Encapsulated by Different Lipids

Mesoporous silica nanoparticles (about 50 mg, no FITC modification) were dispersed in 2 mL water. About 5 μL of 100 mM calcein was added so the final dye concentration was ~250 μM. The solution was divided into 50 μL aliquots and equal volumes of liposomes of different compositions were mixed to form supported bilayers. The supported bilayers were centrifuged and washed three times with 200 μL of 0.25×PBS to remove free calcein. Finally, about 50 μL of 1% SDS buffer solution was added to the precipitated supported bilayers to disrupt the lipid bilayer and release the calcein dye. About 150 μL of 0.25×PBS was then added to make the final volume to be about 200 μL and the tubes were centrifuged at 15000 rpm for about 2 minutes to precipitate silica nanoparticles. About 10 μL from the supernatant was transferred into a quartz microcuvette with a path length of about 1 cm to measure the absorbance at a wavelength of about 500 nm, which is proportional to the amount of calcein dye retained in the mesoporous silica nanoparticle.

Example 8

Quantification of Calcein Release Profile

With the method described above, 200 μL of supported lipid bilayers (DOTAP lipids) with calcein encapsulated inside were prepared. At designated time points, about 20 μL aliquots were taken out into another tube and centrifuged at about 15000 rpm for about 2 minutes. About 10 μL of the supernatant was taken out and transferred into another tube and its fluorescence intensity is denoted to be $F_1$. The fluorescence intensity of the remaining 10 μL is denoted to be $F_2$, which included the other 10 μL of the supernatant and the silica precipitant. The fraction of release was calculated to be $2 \times F_1/(F_1+F_2)$. To measure fluorescence, the dye was released by using 20 μL of 2.5% SDS and the solution was finally dispersed in 500 μL PBS and centrifuged at 15000 rpm for about 5 minutes to precipitate all the silica nanoparticles. About 400 μL of the supernatant was transferred into a fluorescence cuvette and the calcein fluorescence was measured by exciting at a wavelength of about 467 nm and collecting emission at a wavelength of about 517 nm. All experiments were run in triplicate.

As a result, ~90% of the calcein dye was released in 18 days and the rate of releasing gradually decreased with time. A pH-dependent study was also performed and the release was measured after 12 hours. The measured results (see FIG. 4A) indicated that the fraction of calcein dye release significantly increased at lower pH.

Example 9

Concentration Estimation of Calcein Inside Mesoporous Silica Nanoparticles

When 100% DOTAP lipids were used to form supported bilayers, the retained calcein had an absorbance of about 2.5, which corresponded to a concentration of about 45 µM (the extinction coefficient of calcein is ~55,000 M$^{-1}$ cm$^{-1}$ at wavelength of about 500 nm). Because the volume of this final solution was about 200 µL, the retained calcein in silica was then about 9 nmol. The silica mass was about 1.25 mg (i.e., 50 µl of 25 mg/mL). The density of mesoporous silica nanoparticles was estimated to be about 1.07 g/cm. Therefore, the volume of the silica was about 1.17×10$^{-3}$ cm$^3$, and the concentration of calcein inside silica was about 7.7 mM.

The initial calcein concentration in solution was about 250 µM and the final concentration was about 70 µM, with the remaining calcein being inside the silica nanoparticles. Therefore, ~72% of the dye was encapsulated in the particles, and the concentration inside silica was ~110 times higher than that in solution.

Example 10

Lipid Association with Mesoporous Silica Nanoparticles

To measure the amount of lipid associated with silica nanoparticles as a function of lipid concentration, about 20 µL aliquots of 25 mg/mL silica nanoparticles were mixed with 1, 2, 3, 5, 7, 10, 20, and 30 µL of 2.5 mg/mL lipids. The lipids tested included DOPC, DOPS and DOTAP, all containing 5% DHPE-Texas Red labels. The mixtures were centrifuged. The Texas Red absorbance from the supernatant and the silica nanoparticles was measured. As a result, positively charged DOTAP and neutral DOPC liposomes almost quantitatively associated with silica nanoparticles when <20 µg of liposome was used for 0.5 mg silica particles, suggesting a high binding affinity. Further addition of liposomes did not increase association, possibly due to the saturation of the silica surface. Negatively charged DOPS did not associate with silica, which can be attributed to the electrostatic repulsion between them at neutral pH.

Example 11

Colloidal Stability of the Silica/lipid Mixture as a Function of Lipid Concentration Depending on the relative amount of liposome added, silica particles first aggregated at low lipid concentrations to form large aggregates, which disappeared upon adding more liposomes. As characterized by dynamic light scattering, for both DOTAP and DOPC, there was a significant increase in the average size of particles at low liposome contents. Similar observations were also reported for polystyrene beads, where aggregation was attributed to liposome mediated nanoparticle assembly at low lipid concentrations. Therefore, to form supported bilayers with good colloidal stability, excess amount of liposomes (50 µg liposome per 0.5 mg silica) were used.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5. In certain cases, the numerical values as stated for the parameter can take on negative values. In this case, the example value of range stated as "less that 10" can assume negative values, e.g. −1, −2, −3, −10, −20, −30, etc.

Other embodiments of the invention will be apparent to those skilled in the art from consideration of the specification and practice of the invention disclosed herein. It is intended that the specification and examples be considered as exemplary only, with a true scope and spirit of the invention being in dictated by the following claims.

What is claimed is:

1. A protocell nanostructure comprising:
   a negatively charged porous silica particle core comprising a plurality of pores;
   a non-negatively charged fused lipid bilayer on the surface of said porous particle core; and
   a negatively charged cargo component which is loaded into said pores of said porous particle core by combining said cargo with non-negatively charged lipid when said lipid forms said lipid bilayer, wherein said particle core has a particle diameter ranging from about 30 nm to about 3000 nm and is capable of releasing said cargo from the porous particle core at a pH below 7.

2. The protocell nanostructure of claim 1, wherein said cargo is a negatively charged chemotherapeutic drug or nucleic acid.

3. The protocell nanostructure of claim 2, wherein said porous particle core comprises a polymer hydrogel particle or an inorganic particle.

4. The protocell nanostructure of claim 1, wherein the lipid bilayer comprises a phospholipid selected from the group consisting of 1,2-Dioleoyl-3-Trimethylammonium-Propane (DOTAP), 1,2-Dioleoyl-sn-Glycero-3-Phosphocholine (DOPC) or a combination thereof.

5. The protocell nanostructure of claim 2, wherein said lipid bilayer comprises 1,2-Dioleoyl-3-Trimethylammonium-Propane (DOTAP).

6. The protocell nanostructure of claim 2, wherein said lipid bilayer comprises 1,2-Dioleoyl-sn-Glycero-3-Phosphocholine (DOPC).

7. The protocell nanostructure of claim 2, wherein said lipid bilayer comprises a mixture of 1,2-Dioleoyl-3-Trimethylammonium-Propane (DOTAP) and 1,2-Dioleoyl-sn-Glycero-3-Phosphocholine (DOPC).

8. A delivery system for delivering a cargo component from a protocell nanostructure, said delivery system comprising a population of protocell nanostructures, each nanostructure comprising a negatively charged porous silica particle core comprising a plurality of pores, a non-negatively charged fused lipid bilayer on the surface of said porous particle core; and one or more negatively charged cargo components which are loaded into said pores of said porous particle core by combining said cargo with non-negatively charged lipid when said lipid forms said bilayer, wherein said particle core has a particle diameter ranging from about 30 nm to about 3000 nm and is capable of releasing said cargo from said porous particle core at a pH below 7.

9. The delivery system according to claims 8, wherein said cargo is a negatively charged chemotherapeutic drug or nucleic acid.

10. The delivery system according to claim 8, wherein said porous particle core comprises a polymer hydrogel particle or an inorganic particle.

11. The delivery system according to claim 8, wherein the lipid bilayer comprises a phospholipid selected from the group consisting of 1,2-Dioleoyl-3-Trimethylammonium- Propane (DOTAP), 1,2-Dioleoyl-sn-Glycero-3-Phosphocholine (DOPC) or a combination thereof.

12. The delivery system according to claim 9, wherein said lipid bilayer comprises 1,2-Dioleoyl-3-Trimethylammonium-Propane (DOTAP).

13. The delivery system according to claim 9, wherein said lipid bilayer comprises 1,2-Dioleoyl-sn-Glycero-3-Phosphocholine (DOPC).

14. The delivery system according to claim 9, wherein said lipid bilayer comprises a mixture of 1,2-Dioleoyl-3-Trimethylammonium-Propane (DOTAP) and 1,2-Dioleoyl-sn-Glycero-3-Phosphocholine (DOPC).

* * * * *